(12) United States Patent
Ito et al.

(10) Patent No.: US 8,303,548 B2
(45) Date of Patent: Nov. 6, 2012

(54) INJECTION DEVICE

(75) Inventors: Toru Ito, Hiroshima (JP); Raita Uematsu, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 262 days.

(21) Appl. No.: 12/227,452

(22) PCT Filed: May 18, 2007

(86) PCT No.: PCT/JP2007/060277
§ 371 (c)(1),
(2), (4) Date: Nov. 18, 2008

(87) PCT Pub. No.: WO2007/136016
PCT Pub. Date: Nov. 29, 2007

(65) Prior Publication Data
US 2009/0118679 A1  May 7, 2009

(30) Foreign Application Priority Data
May 19, 2006  (JP) .................................. 2006-140441

(51) Int. Cl.
*A61M 5/315* (2006.01)
(52) U.S. Cl. .................... 604/218; 604/164.08; 604/263; 604/187
(58) Field of Classification Search .................. 604/181, 604/187, 110, 263, 164.08, 218, 192
See application file for complete search history.

(56) References Cited

U.S. PATENT DOCUMENTS

| | | | |
|---|---|---|---|
| 1,712,070 A | 5/1929 | Cressler | |
| 2,904,043 A | 9/1959 | Friedman | |
| 3,811,441 A | 5/1974 | Sarnoff | |
| 3,838,690 A | 10/1974 | Friedman | |
| 4,723,945 A | 2/1988 | Theiling | |
| 5,013,301 A * | 5/1991 | Marotta et al. | 604/197 |
| 5,024,660 A * | 6/1991 | McNaughton | 604/110 |
| 5,344,407 A * | 9/1994 | Ryan | 604/192 |
| 6,126,644 A | 10/2000 | Naganuma et al. | |
| 2002/0169421 A1* | 11/2002 | McWethy et al. | 604/192 |
| 2005/0033242 A1* | 2/2005 | Perez et al. | 604/198 |
| 2005/0113754 A1 | 5/2005 | Cowan | |
| 2007/0100294 A1 | 5/2007 | Sugita et al. | |

FOREIGN PATENT DOCUMENTS

| | | |
|---|---|---|
| AU | 642 002 | 10/1993 |
| EP | 0 904 792 | 3/1999 |
| FR | 2 377 207 | 8/1978 |

(Continued)

*Primary Examiner* — Kevin C Sirmons
*Assistant Examiner* — Edelmira Bosques
(74) *Attorney, Agent, or Firm* — Hamre, Schumann, Mueller & Larson, P.C.

(57) ABSTRACT

An injection device includes: a syringe 2 including a barrel 21 including a cylindrical barrel body 21a and a nozzle 21b provided at a front end of the barrel body so as to be communicated with the barrel body, a gasket 23 slidable in the barrel, and a plunger 24 connected with the gasket and capable of being placed into and removed from the barrel through a rear end opening of the barrel; a finger flange 25 provided in the vicinity of the rear end portion of the barrel body and molded integrally with or separately from the barrel body; and a holder 3 having an inner diameter that allows the barrel to be inserted in a bore of the holder, attached to the barrel, and including a spiral protrusion 31a formed on the inner surface of a portion of the holder disposed around the nozzle.

8 Claims, 13 Drawing Sheets

FOREIGN PATENT DOCUMENTS

| | | |
|---|---|---|
| JP | 60-234670 | 11/1985 |
| JP | 10-155905 | 6/1998 |
| JP | 10-174718 | 6/1998 |
| JP | 2007-117379 | 5/2007 |
| WO | 94/03392 | 2/1994 |
| WO | 95/07672 | 3/1995 |
| WO | 01/85237 | 11/2001 |
| WO | 03/022457 | 3/2003 |

* cited by examiner

INJECTION DEVICE

TECHNICAL FIELD

The present invention relates to an injection device including a syringe and a holder attached to the syringe. More particularly, the present invention relates to an injection device including a syringe filled with a drug solution or the like in advance (hereinafter, referred also to as a "prefilled syringe") and a holder attached to the syringe.

BACKGROUND ART

In a prefilled syringe, a barrel is filled with a predetermined amount of drug solution in advance. A nozzle from which a liquid can be discharged is provided at a front end of a barrel body. A rubber cap or the like is put on the nozzle, and thus an opening of the nozzle is closed. A gasket is inserted slidably into the barrel body through a rear end opening of the barrel body. The drug solution or the like is contained in a space enclosed with the gasket and the barrel at a portion closer to a front end than the gasket. Since the gasket is in intimate contact with the inner surface of the barrel, the liquid-tightness of the space is maintained. When using the syringe, the drug solution can be discharged from the nozzle by removing the rubber cap from the nozzle, and pressing a plunger connected with the gasket into the barrel. By using such a prefilled syringe, time and effort required in administering medicines to patients or in mixing medicines can be reduced.

In many cases, the barrel is made of a synthetic resin. However, depending on the type of drug solution to be charged in the barrel, the barrel needs to be made of glass. In that case, unlike a barrel made of a synthetic resin, it is difficult to form a large finger flange due to the properties of glass. As a result, it is difficult to hook fingers on the flange, and thus a stable operation becomes difficult. It is also necessary to prevent breakage of the barrel during storage and transportation.

Patent document 1 discloses an injection device including a syringe and a syringe holder attached to the syringe. As shown in FIG. 14, a syringe holder 206 has an inner diameter that allows the syringe holder 206 to be attached to a cylinder tube 200 of the syringe. The syringe holder 206 includes a cylindrical holder body 207 having a length equal to the cylinder tube 200, and a finger flange 273 formed on a rear end side of the holder body 207. The finger flange 273 is formed such that its width is larger than that of a lug 222 formed on the cylinder tube 200. The syringe holder 206 includes also a fixing member 88. By sandwiching the lug 222 between the fixing member 88 and the finger flange 273, the holder body 207 is fixed to the cylinder tube 200. The sandwiching of the lug 222 is maintained by engaging first engagement protrusions 275 of the finger flange 273 with second engagement protrusions 284 of the fixing member 88.

In the injection device shown in FIG. 14, an injection needle holding portion configured of a spiral protrusion (not shown) is formed on an inner surface 271 of a front end portion of the holder body 207. Since an injection needle is fixed to the holding portion, the injection needle is prevented from dropping off from the cylinder tube 200 even when a high pressure is applied to the injection needle at the time of discharging a highly viscous medicine. Patent document 1: JP H10-155905 A

DISCLOSURE OF INVENTION

Problem to be Solved by the Invention

In the injection device described in Patent document 1, however, the nozzle 221 cannot be inserted into, for example, a slit formed on a disk-shaped valve provided with a mixed injection port or the like, while an injection needle can be fixed firmly. This is because the nozzle 221 at the front end of the cylinder tube 200 is covered with the holder body 207. Thus, in the injection device described in Patent document 1, since the holder body 207 is placed on the cylinder tube 200, a disadvantage of limitation in the application range of the injection device is caused.

Further, from the viewpoint of operability, it is preferable that the injection device is provided with the finger flange 273 regardless of whether a drug solution to be discharged has a high or low viscosity.

In the injection device described in Patent document 1, however, since the holder body 207 and the finger flange 273 are molded integrally and they are inseparable from each other, the holder body 207 cannot be removed solely from the syringe while leaving the finger flange 273 on the syringe. That is, Patent document 1 fails to disclose an idea that the holder body 207 is attached to and detached from the cylinder tube 200 if necessary.

The present invention provides an injection device in which a holder body can be attached to and detached from a syringe, and can be operated stably even in a state where the holder body is detached from the syringe.

Means for Solving Problem

The injection device of the present invention includes: a syringe including a barrel including a cylindrical barrel body and a nozzle provided at a front end of the barrel body so as to be communicated with the barrel body, a gasket slidable in the barrel, and a plunger connected with the gasket and capable of being placed into and removed from the barrel through a rear end opening of the barrel; a finger flange provided in the vicinity of a rear end portion of the barrel body and molded integrally with or separately from the barrel body; a holder having an inner diameter that allows the barrel to be inserted into a bore of the holder, attached to the barrel, and including a spiral protrusion formed on the inner surface of a portion around the nozzle; and an engagement structure capable of keeping a state in which the holder is attached to the barrel and releasing the attachment.

DESCRIPTION OF THE INVENTION

Figure 1:
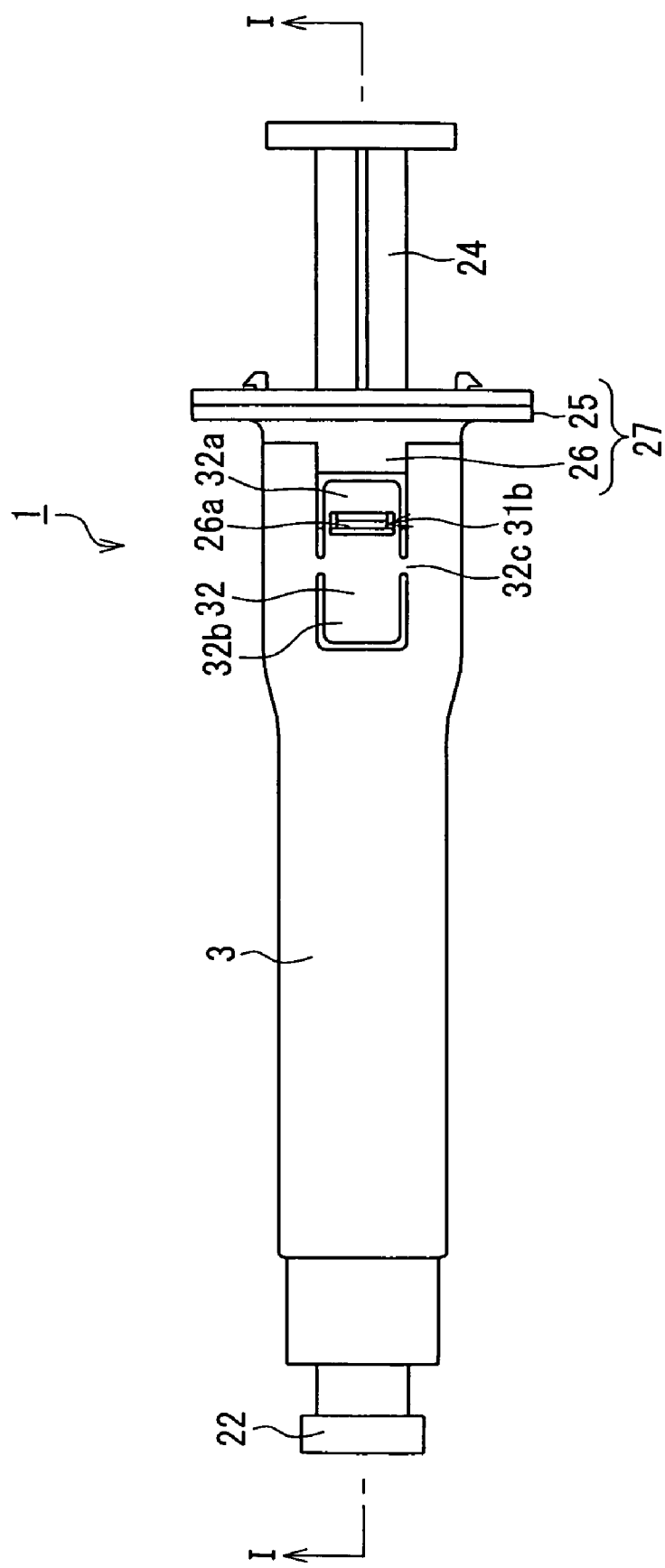
FIG. 1 is a side view showing an example of an injection device of Embodiment 1.

In one example of the injection device of the present invention, the syringe may be a so-called prefilled syringe that further includes a liquid contained in a space enclosed with a gasket and a barrel at a portion closer to a front end than the gasket.

In one example of the injection device of the present invention, when the barrel is made of glass for example, the finger flange is normally molded separately from the barrel body.

In one preferred example of the injection device of the present invention, the barrel body includes, at a rear end portion thereof, an annular large-diameter portion having a larger outer diameter than its adjacent portion. The injection device includes an erected portion that is erected from the finger flange and that is attached to the barrel. It is preferable that the erected portion has a substantially cylindrical shape, for example. In this case, it is preferable that the inner diameter at a part of the erected portion is larger than the outer diameter of the large-diameter portion so that the large-diameter portion can be placed into a bore of the erected portion.

In one preferred example of the injection device of the present invention, an engagement structure can connect the holder and the erected portion with each other. More specifically, the engagement structure includes, for example, an opening and an engagement hook. The engagement hook can be engaged with the opening. The opening is formed on either the holder or the erected portion. On the other hand, the engagement hook is formed on either the holder or the erected portion on which the opening is not formed. It is preferable that the opening is formed on the rear end side of the holder, and the engagement hook is formed on the erected portion. In this case, the length of the erected portion (the length in the same direction as the length of the injection device in the longitudinal direction) can be decreased. Thus, the interior of the barrel can be seen easily when the holder is detached from the syringe, and thus preferable.

In one preferred example of the injection device of the present invention, the holder includes, on a rear end side thereof, a bendable strip. The bendable strip is supported due to linking of its central portion to the other part of the holder. It is preferable that the opening is formed on the bendable strip at a portion closer to the finger flange than the support portion. In this case, the length of the erected portion (the length in the same direction as the length of the injection device in the longitudinal direction) can be decreased in comparison with the case where the opening is formed on the bendable strip at a portion apart from the finger flange than the support portion. Therefore, the interior of the barrel can be seen easily when the holder is detached from the syringe, and thus preferable.

In one preferred example of the injection device of the present invention, an outer surface of the bendable strip and the peripheral surface of the holder around the bendable strip are in the same circumferential plane.

In one preferred example of the injection device of the present invention, when the engagement hook is in engagement with the opening, a rear end surface of the holder and a surface of the finger flange that faces the rear end surface of the holder are apart from each other.

In one preferred example of the injection device of the present invention, the inner diameter of the holder is smaller at the front end side than at the rear end side.

In one preferred example of the injection device of the present invention, the erected portion includes a cantilever arm having a free end on the front end side of the erected portion. In this case, it is preferable that an engagement hook is formed on the free end side of the cantilever arm. The engagement hook is protruded outwardly with respect to the cantilever arm.

In one preferred example of the injection device of the present invention, the holder includes, at a portion closer to the rear end than the opening, a notch from which a portion of the cantilever arm can be exposed. In this case, engagement between the opening and the engagement hook can be released by pressing the portion of the cantilever arm exposed from the notch.

In one preferred example of the injection device of the present invention, a pressing protrusion protruded outwardly with respect to the cantilever arm is formed on the cantilever arm at the portion exposed from the notch.

In one preferred example of the injection device of the present invention, the finger flange includes a first member linked to the erected portion and having a first hole and a second member having a second hole. The first hole communicates with the bore of the barrel. The finger flange also includes a holding structure for keeping a state in which the second member is disposed on a side of the first member opposite to the side facing the erected portion so that the second hole communicates with the first hole. The holding structure includes an engagement opening formed on either the first member or the second member and a protrusion formed on either the first member or the second member on which the engagement opening is not formed and capable of engaging with the engagement opening.

In one preferred example of the injection device of the present invention, the first and the second members are connected with each other via a hinge.

In one preferred example of the injection device of the present invention, an engagement opening is formed on the first member and a protrusion is formed on the second member. More specifically, the protrusion is erected from the surface of the second member that faces the first member, and a hook is provided at the tip of the protrusion so as to be in contact with the surface of the first member that faces the second member.

Hereinafter, the present invention will be described in detail with reference to the drawings.

Embodiment 1

In Embodiment 1, an example of the injection device of the present invention will be described.

Figure 2:
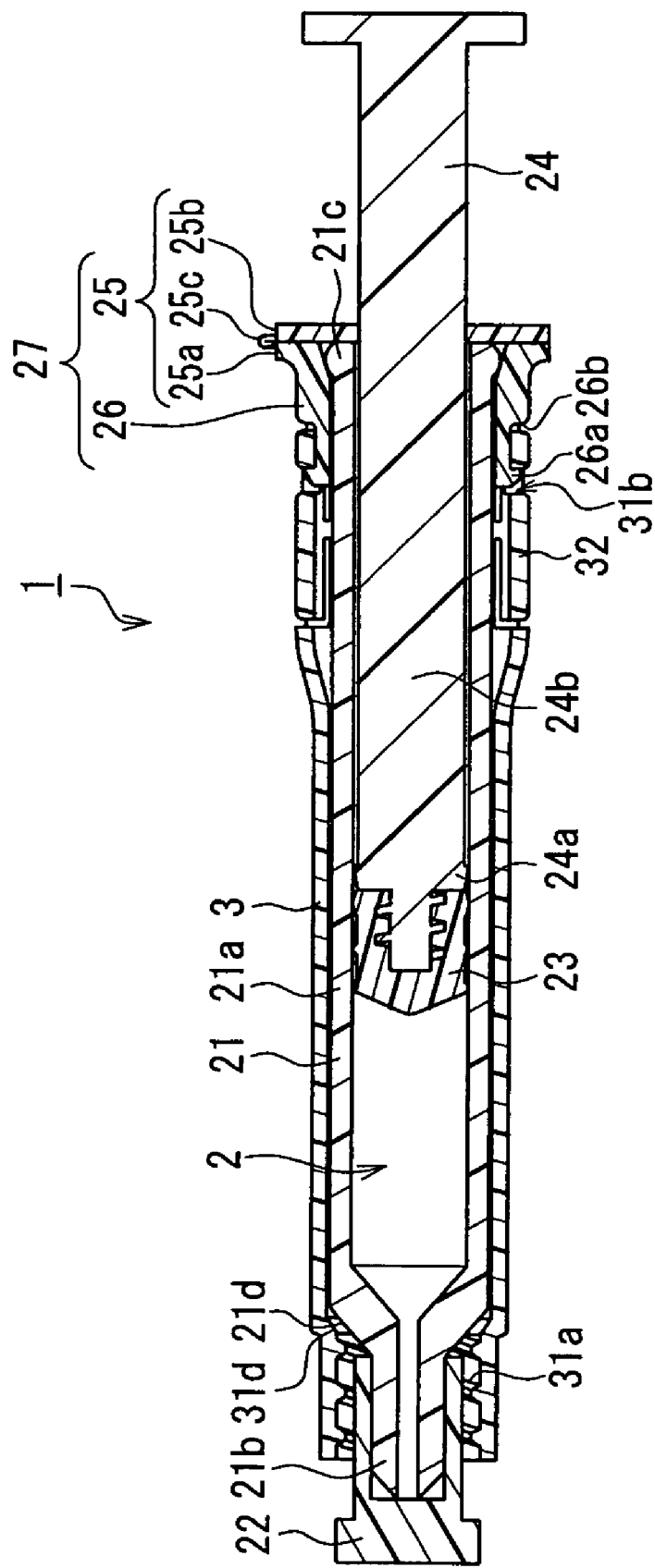
FIG. 2 is a cross-sectional view showing the injection device shown in FIG. 1, taken along a line I-I.
Figure 3:
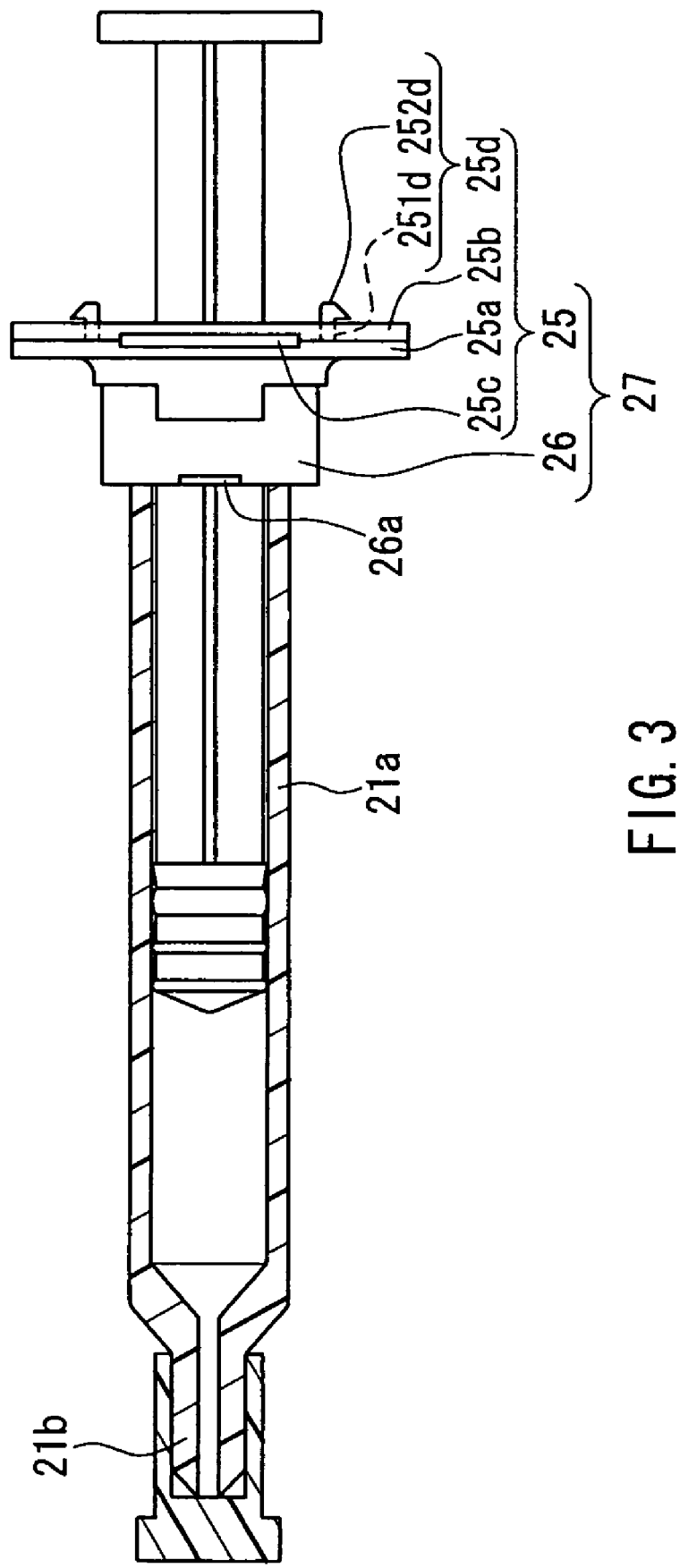
FIG. 3 is a partial cross-sectional view showing the injection device shown in FIG. 1 in a state where the holder is removed.
Figure 4A:
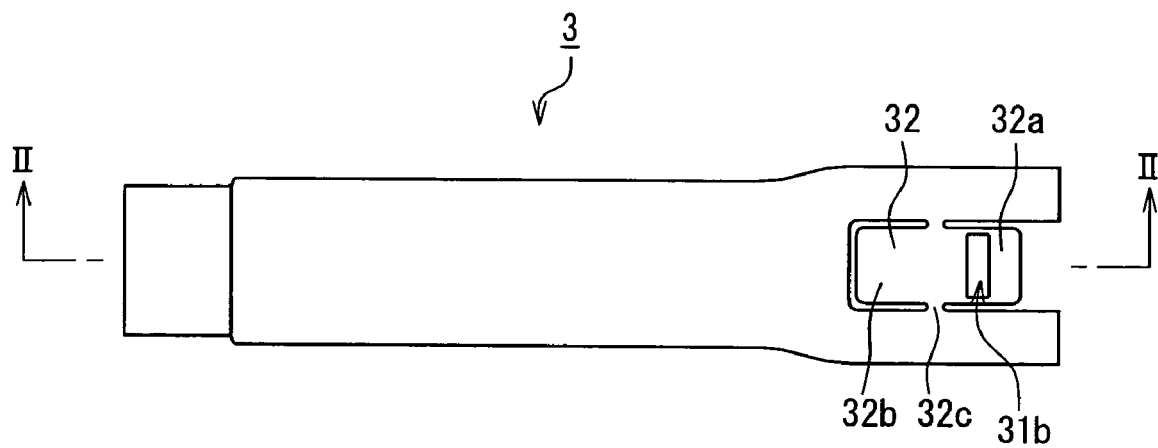
FIG. 4A is a side view showing the holder that constitutes the injection device shown in FIG. 1.
Figure 4B:
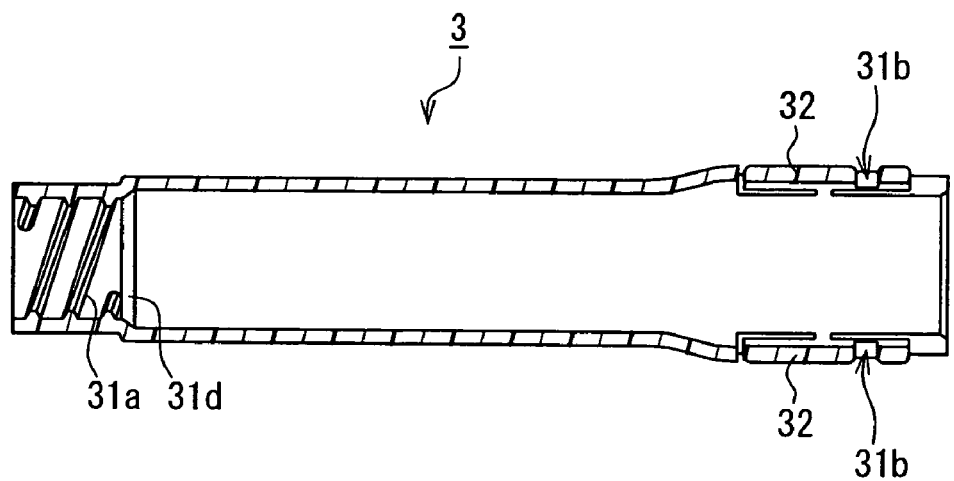
FIG. 4B is a cross-sectional view showing the holder shown in FIG. 4A, taken along a line II-II.

FIG. 1 is a side view showing an example of the injection device of the present invention. FIG. 2 is a cross-sectional view showing the injection device shown in FIG. 1, taken along a line I-I. FIG. 3 is a partial cross-sectional view showing the injection device in a state where the holder is detached. FIG. 4A is a side view showing the holder constituting the injection device shown in FIG. 1, and FIG. 4B is a cross-sectional view showing the holder shown in FIG. 4A, taken along a line II-II.

As shown in FIGS. 1 and 2, a barrel 21 of a prefilled syringe 2 constituting an injection device 1 of the present embodiment is filled with a predetermined amount of drug solution or the like (not shown) in advance. A nozzle 21b from which the drug solution or the like can be discharged is formed at a front end of a cylindrical barrel body 21a. The inner and the outer diameters of the nozzle 21b are smaller than the inner and the outer diameters of the barrel body 21a, respectively. A cap 22 made of an elastic material such as rubber is put on the nozzle 21b, and thus an opening of the nozzle 21 is closed. A gasket 23 is inserted slidably into the barrel 21 through a rear end opening of the barrel 21. The drug solution or the like is contained in a space enclosed with the gasket 23, the barrel 21 at a portion closer to the front end than the gasket 23, and the cap 22. Since the gasket 23 is in intimate contact with the inner surface of the barrel 21, the liquid-tightness of the space is maintained. A plunger 24 is connected with the gasket 23, and it can be placed into and removed from the barrel 21 through the rear end opening of the barrel 21. When using the device, the drug solution can be discharged from the nozzle 21b by removing the rubber cap 22 from the nozzle 21b and pressing the plunger 24 into the barrel 21.

A holder 3, which is attached to the barrel 21 and arranged to cover the outer periphery of the barrel 21, has an inner diameter that allows the barrel body 21a to be placed in the holder 3. A spiral protrusion 31a is formed on the inner surface of the holder 3 at a portion located around the nozzle 21b. The spiral protrusion 31a is formed so that it can be screwed with, for example, an injection needle or a female luer constituting a part of a three-way cock or the like. Specifically, the spiral protrusion 31a can be screwed with an annular protrusion formed on the outer periphery of an end of a hub constituting the injection needle, or an annular protrusion formed on the outer periphery of an end of the female luer. Therefore, the injection needle or the female luer attached to the nozzle 21b is fixed to the nozzle 21b because the nozzle 21b is inserted into its bore. At the same time, the needle or the female luer is fixed also to the holder 3 by the screwing. As a result, the injection needle, the female luer or the like is prevented from dropping off from the nozzle 21b even if a high pressure is applied thereto.

As shown in FIG. 3, in the present embodiment, the finger flange 25 is molded separately from the barrel body 21a but is molded integrally with a substantially cylindrical erected portion 26 attached to the rear end side of the barrel body 21a.

FIGS. 3 and 2 clearly show attachment of a structure 27 including the finger flange 25 and the erected portion 26 to the barrel body 21a. The finger flange 25 includes a first member 25a substantially in a plate shape, a second member 25b substantially in a plate shape, and a hinge 25c for connecting the first and the second members. The hinge 25 is bendable, and the first member 25a and the second member 25b are arranged in parallel and are in contact with each other. This state is kept by, for example, a holding structure described below.

Figure 5A:
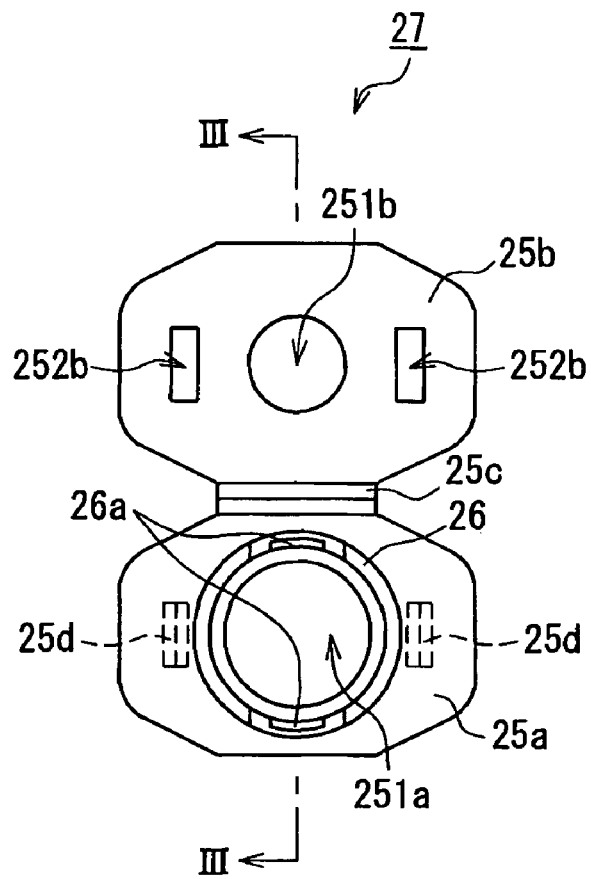
FIG. 5A is a view showing a structure including a finger flange and an erected portion and constituting the injection device of FIG. 1 from the axial direction of the barrel.

As shown in FIG. 5A, a pair of engagement openings 252b is formed on the second member 25b that constitutes the finger flange. In contrast, a pair of protrusions 25d, which corresponds to the pair of the engagement openings 252b, is formed on the first member 25a. As shown in FIG. 3, each of the protrusions 25d is erected at a substantially right angle from a surface of the first member 25a that faces the second member 25b. Further, each of the protrusions 25d includes a leg portion 251d and a hook 252d provided at the tip of the leg portion. The length of the leg portion 251d is substantially equal to the thickness of the second member 25b.

In this manner, the holding structure constituting the finger flange 25 is configured of the engagement openings 252b and the protrusions 25d. The contact between the first member 25a and the second member 25b is kept by inserting the protrusions 25d into the engagement openings 252b, and bringing the hooks 252d so as to face the surface of the second member 25b opposite to the surface facing the first member 25a.

As shown in FIGS. 3 and 5A, the erected portion 26 is linked to the first member 25a. A first hole 251a is formed on a portion between the pair of the protrusions 25b in a plan view of the first member 25a along the axial direction of the erected portion 26 (see FIG. 5A). It is preferable that the diameter of the first hole 251a is substantially equal to or slightly larger than the outer diameter of a large-diameter portion 21c (see FIG. 2) of the barrel body 21a. Further, it is preferable that the inner diameter at a part of the erected portion 26 is substantially equal to or larger than the outer diameter of the large-diameter portion 21c. In the example shown in FIG. 2, the inner diameter of the erected portion 26 at the base end portion is substantially equal to or larger than the large-diameter portion 21c. In this case, as shown in FIG. 2, the large-diameter portion 21c can be placed into the bore of the erected portion 26. Further, the inner diameter at a part of the erected portion 26 is substantially equal to or larger than the outer diameter of the large-diameter portion 21c, and the inner diameter at the other part of the erected portion 26 is smaller than the outer diameter of the large-diameter portion 21c. Thus, during the process for assembling the injection device of the present embodiment, the structure 27, which is attached to the barrel body 21a from the end of the nozzle 21b side and slid to the rear end side of the barrel body 21a, is prevented from passing through the large-diameter portion 21c and dropping off from the rear end side of the barrel body 21a.

As shown in FIG. 5A, a second hole 251b is formed on the second member 25b. The second hole 251b is formed on a portion between the pair of the engagement openings 252b. It is preferable that the diameter of the second hole 251b is slightly smaller than the outer diameter of a front end portion 24a (see FIG. 2) of the plunger 24 but larger than the outer diameter of a portion 24b (see FIG. 2) located on the back side with respect to the front end 24a and is inserted in the barrel. In this case, it is possible to slide the plunger 24 smoothly, and the plunger 24 is prevented from dropping off.

As shown in FIG. 5A, the finger flange 25 extends particularly in a predetermined radial direction. Specifically, the finger flange 25 does not extend greatly in a direction from the center of the first hole or the center of the second hole to the hinge 25c and in the opposite direction. The finger flange 25 extends greatly in a direction orthogonal to the direction from the center of the first hole to the hinge 25c, so that it is possible to hook fingers on the finger flange 25 adequately. However, in the present embodiment, the shape of the finger flange is not limited to the shape described with reference to FIG. 5A. For example, the outer shape of the finger flange 25 may be substantially circular when it is seen along the axial direction of the erected portion 26.

Next, an engagement structure capable of keeping a state in which the holder 3 is attached to the barrel 21 and releasing the attachment will be described.

As shown in FIGS. 1 and 2, the engagement structure is configured of openings 31 formed by forming through holes that penetrate the cylinder wall of the holder 3 in the thickness direction, and engagement hooks 26a that are formed on the erected portion 26 and can be engaged with the openings 31b.

Figure 5B:
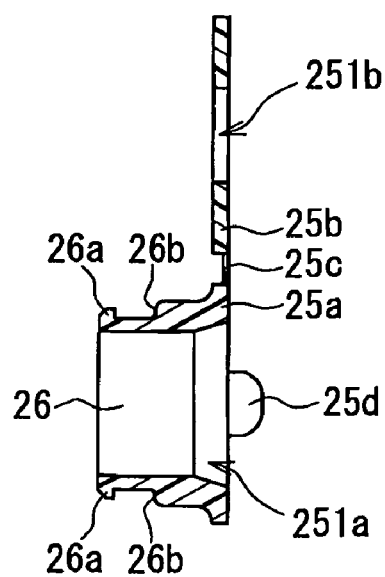
FIG. 5B is a cross-sectional view showing the structure shown in FIG. 5A, taken along a line III-III.

As shown in FIGS. 5A and 5B, it is preferable that the engagement hooks 26a are formed on the outer periphery of the front end tip of the erected portion 26. Though there is no particular limitation for the length of the erected portion 26 in the axial direction, the longer erected portion 26 is not preferred because the interior of the barrel will be difficult to observe. Thus, it is not preferable that the erected portion 26 is too long in the axial direction. On the other hand, when the erected portion 26 is too short in the axial direction, the positions at which the engagement hooks 26a are provided get too close to the finger flange 25. In this case, at the time of releasing the engagement, the hand holding the finger flange 25 (e.g., right hand) and the hand releasing the engagement by the engagement structure (e.g., left hand) get too close to each other, and it becomes difficult to release the engagement. Thus, it is preferable that the engagement hooks 26a are formed at the front end tip side of the erected portion 26 located apart from the finger flange 25, and it is preferable that the length of the erected portion 26 in the axial direction is set in view of both the ease of releasing the engagement and the visibility within the barrel.

There is no particular limitation for the number of the engagement hooks 26a as long as it matches the number of the openings 31b. Considering that the engagement is released with one hand, it is preferable that one or two engagement hooks are provided. When the stability of the engagement is considered, it is preferable that two engagement hooks are provided as shown in FIG. 5A. From the view point of operability of releasing the engagement, it is further preferable that the pair of the engagement hooks 26a are formed at positions symmetrical to each other about the central axis of the erected portion 26.

There is no particular limitation for the positional relationship between the engagement hooks 26a and the protrusions 25d. For example, like the example shown in FIG. 5A, it is preferable that the pair of the engagement hooks 26a is formed on a straight line that is orthogonal to a straight line passing through the center of each of the protrusions 25d and the center of the first hole 251a and also that passes through the center of the first hole 251a, when the structure 27 is seen along the axial direction of the erected portion 26. That is, it is preferable that the engagement hooks 26a and the protrusions 25d are apart from each other by a rotation angle of about 90 degrees.

In the example shown in FIGS. 1 and 3, the outer diameter of the erected portion 26 at the front end side portion is smaller than the inner diameter of the holder 3 at the rear end side portion. Thus, the engagement hooks 26a engage with the openings 31b from inside the holder 3.

As shown in FIG. 1, it is preferable that the rear end surface of the holder 3 and the surface of the finger flange 25 that faces the rear end surface of the holder 3 are apart from each other when the engagement hooks 26a are in engagement with the openings 31b. If they are in contact with each other, the rear end portion of the holder 3 may be also held by the fingers holding the finger flange 25. Consequently, sliding of the holder 3 in the front end direction, which is carried out after the engagement between the engagement hooks 26a and the openings 31b is released, may be hindered. Accordingly, as shown in FIGS. 5B and 2, it is preferable that the outer diameter of the erected portion 26 at the base end side portion is larger than that at the front end side portion, and the erected portion 26 includes a step surface 26b with which the rear end surface of the holder 3 comes into contact when the engagement hooks 26a are in engagement with the openings 31b. In this case, the state in which the engagement hooks 26a are engaged with the openings 31b can be stabilized, and the sliding operation of the holder 3, which is carried out after the engagement is released, can be carried out with ease.

As shown in FIGS. 1, 4A and 4B, the holder 3 includes, on a rear end side thereof, a pair of bendable strips 32. On each of the bendable strips 32, the opening 31b with which the engagement hook 26a engages is formed. A central portion of each of the bendable strips 32 is linked to the other parts of the holder 3 and supports the bendable strip 32. On each of the bendable strips 32, the opening 31b is formed on a portion 32a that is closer to the finger flange than the support portion. A portion of each of the bendable strips 32 that is apart from the finger flange 25 than the support portion 32c functions as an operation strip 32b. By pressing each of the operation strips 32b in a direction toward the central axis of the holder 3 so as to bend each of the bendable strips 32 with the support portion 32c as a fulcrum, a space between the portions 32a of the bendable strips 32 that are closer to the finger flange 5 than the support portions 32c widens. As a result, engagement between each of the openings 31b and the corresponding engagement hook 26a is released.

In this case, as shown in FIG. 2, it is necessary to provide a gap having a predetermined length between each of the bendable strips 32 and the barrel body 21a in order to bend the bendable strips 32 as described above. However, if a gap between the inner surface of the holder 3 and the barrel body 21a is too large, the barrel body 21a wobbles within the holder 3. Thus, as shown in FIGS. 2 and 4B, it is preferable that the inner diameter of the holder 3 at the front end side is smaller than at the rear end side. More specifically, it is preferable that the inner diameter of the holder 3 at a portion closer to the front end than the bendable strips 32 is smaller than at a portion closer to the rear end than the bendable strips 32. Furthermore, it is preferable that the inner diameter of the holder 3 at the portion closer to the front end than the bendable strips 32 is slightly larger than the outer diameter of the barrel body 21a at a portion closer to the front end side than the large-diameter portion 21c. In this case, it is possible to engage each of the bendable strips 32 with the opening 31b and to release the engagement, while the prefilled syringe is prevented from wobbling in the radial direction within the holder 3.

Further, as shown in FIGS. 1, 4A and 4B, it is preferable that the outer surfaces of the bendable strips 32 and the peripheral surface of the holder 3 around the bendable strips 32 are in the same circumferential plane since the engagement between the engagement hooks 26a and the openings 31b can be prevented from being released unintentionally.

As shown in FIG. 4B, the inner diameter of the holder 3 at the portion on which the spiral protrusion 31a is formed is smaller than at the rear end side portion. Therefore, the inner surface of the holder 3 includes a step surface 31d for connecting the portion on which the spiral protrusion 31a is formed and its adjacent portion. In contrast, as shown in FIG. 2, the outer surface of the barrel 21 includes a step surface 21d for connecting the nozzle 21b and the barrel body 21a. These step surfaces 21d and 31d mutually function to control the movement of the barrel 21 in the axial direction within the holder 3.

As described above, in the example of the injection device of the present embodiment, the holder 3 can be freely attached to and detached from the prefilled syringe 2. As shown in FIG. 3, in a state where the engagement by the engagement structure is released and the holder 3 is detached from the prefilled syringe, the nozzle 21b can be inserted into an insertion hole formed at a valve provided with a mixed injection in advance. Further, a mechanism for keeping a state in which the finger flange 25 is provided in the vicinity of the rear end portion of the barrel and a mechanism for keeping a state in which the holder is attached to the barrel are independent from each other. Thus, even if the holder 3 is detached from the prefilled syringe 2, the finger flange 25 is kept to be provided on the barrel 21. Accordingly, in the injection device of the present embodiment, it is possible to always hook fingers on the finger flange 25 tightly, and the device can be operated stably.

There is no particular limitation for the material of the barrel 21. For example, a resin or glass having high transparency and high chemical resistance is preferable. It is preferable that the resin is cyclic polyolefin, polycarbonate, polyethylene terephthalate, polypropylene, polyethylene naphthalate or the like. It is preferable that the nozzle 21b includes a surface with a 6% taper defined in ISO 594-1.

There is no particular limitation for the material of the holder 3. It is preferable that the material is, for example, a lightweight resin having high transparency. It is preferable that the resin is polycarbonate, polypropylene, polyethylene naphthalate, polyethylene terephthalate or the like. The material of the structure 27 only needs to be similar to the material of the holder 3. It is preferable that the spiral protrusion formed on the holder 3 is a spiral protrusion defined in ISO 594-2.

There is no particular limitation for the material of the plunger. It is preferable that the material is, for example, a resin such as polypropylene or polyethylene.

There is no particular limitation for the material of the gasket. It is preferable that the material is, for example, a butyl rubber, a styrenic thermoplastic elastomer or the like.

There is no particular limitation for the material of the cap. It is preferable that the material is, for example, a butyl rubber, a styrenic thermoplastic elastomer or the like.

Next, an example of method of assembling the injection device of the present embodiment will be described with reference to FIG. 2.

First, the cap 22 is put on the nozzle 21b of the barrel 21. Then, after the barrel 21 is filled with a predetermined amount of drug solution or the like, the gasket 23 is inserted into the barrel 21 through the rear end opening of the barrel 21. In this way, the drug solution is held in an enclosed space. It is necessary to control strictly the hygienic conditions or the like of the atmosphere in which these steps are carried out. The following steps, which are performed after charging the drug solution, may be performed in an environment where the hygienic conditions are controlled somewhat loosely.

Next, the structure 27 is attached to the barrel 21. The structure 27 is attached to the barrel 21 in a state where the protrusions 25d are not in engagement with the openings 252b (see FIGS. 3 and 5A). Further, the structure 27 is attached to the barrel 21 by inserting sequentially the barrel 21 into the first hole 251a and then into the bore of the erected portion 26 from the nozzle 21b side. The structure 27 is placed on the rear end portion of the barrel 21, and the protrusions 25d are engaged with the engagement openings 252b by bending the hinge 25c (see FIGS. 3 and 5A). Subsequently, the barrel 21 to which the rubber cap 22 and the structure 27 are attached is inserted into the holder 3, and the engagement hooks 26a are engaged with the openings 31b. The barrel 21 is inserted into the holder 3 by inserting the barrel 21 through the rear end opening of the holder 3 from the nozzle 21b side. Thereafter, the plunger 24 is connected with the gasket 23. In this way, the injection device 1 of the present embodiment can be assembled.

The example of the injection device of the present embodiment has been described with reference to FIGS. 1 to 5B. The injection device of the present invention is not limited to this example. For example, from the viewpoint of reducing the number of parts and molding steps, it is preferable that the first member 25a and the second member 25b are connected with each other via the hinge 25c (see FIG. 5A). However, the first member 25a and the second member 25b are not necessarily connected with each other.

Figure 6:
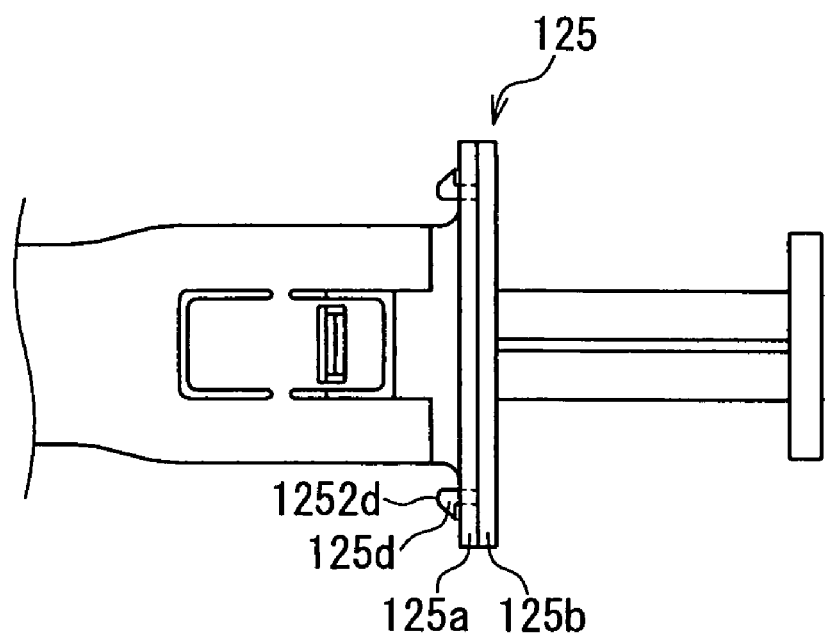
FIG. 6 is a side view showing a part of another example of the injection device of Embodiment 1.

In the example shown in FIGS. 1 to 3, the protrusions 25d are provided on the first member 25a and the engagement openings are formed on the second member 25b. However, as shown in FIG. 6, protrusions 125d may be provided on a second member 125b, and engagement openings may be formed on a first member 125a. In this case, such a configuration is preferable because hooks 1252d of the protrusions 125d provide an antislip function when fingers are hooked on the finger flange 125.

In the example shown in FIG. 2, the surface of the first member 25a that faces the second member 25b and the rear end surface of the barrel 21 are substantially in the same plane. However, the large-diameter portion 21c may be protruded from the surface of the first member 25a that faces the second member 25b, or the large-diameter portion 21c may be sandwiched between the first member 25a and the second member 25b. Further, the large-diameter portion 21c may be retracted into the front end side of the erected portion 26.

Figure 7:
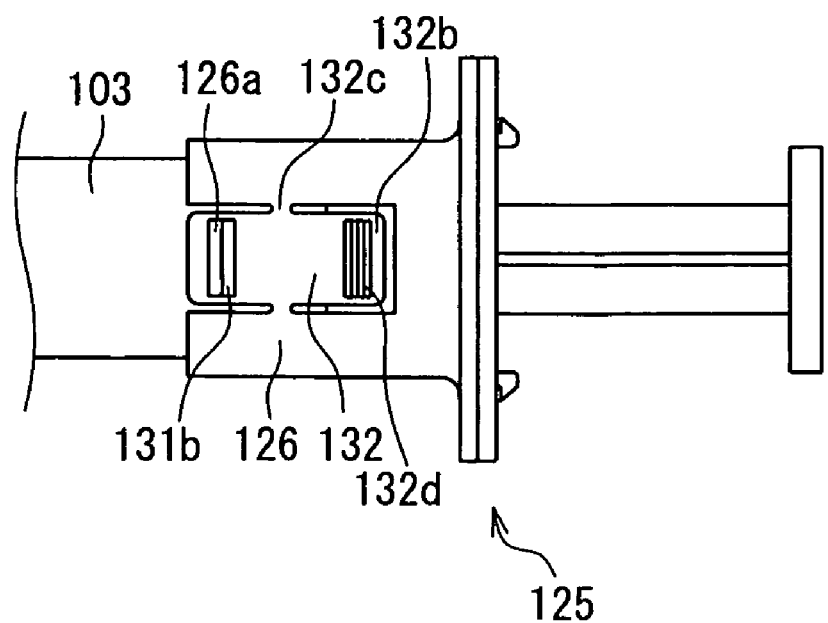
FIG. 7 is a side view showing a part of still another example of the injection device of Embodiment 1.

Further, as shown in FIG. 7, the bendable strips 132 may constitute a part of an erected portion 126. In this case, engagement hooks 126a are provided on, for example, the outer surface of a holder 103. Openings 131b with which the engagement hooks 126a engage may be formed on portions of the bendable strips 32 that are apart from a finger flange 125 than support portions 132c of the bendable strips 132, or portions closer to the finger flange 125 than the support portions 132c.

In the example shown in FIG. 7, the portions of the bendable strips 132 that are closer to the finger flange 125 than the support portions 132c function as operation strips 132b. In this case, from the viewpoint of carrying out the operation with ease, it is preferable that an operation protrusion 132d is provided on the outer surface of each of the operation strips 132b. Similarly, in the injection device of Embodiment 1, an operation protrusion may be provided on the outer surface of each of the operation strips 32b.

Embodiment 2

In Embodiment 2, another example of the injection device of the present invention will be described.

The injection device of the present embodiment has a configuration similar to the injection device of Embodiment 1 except that a structure including a finger flange and an erection portion, a holder and an engagement structure are different. Due to the similar configuration, the injection device of the present embodiment presents similar effects.

Figure 8:
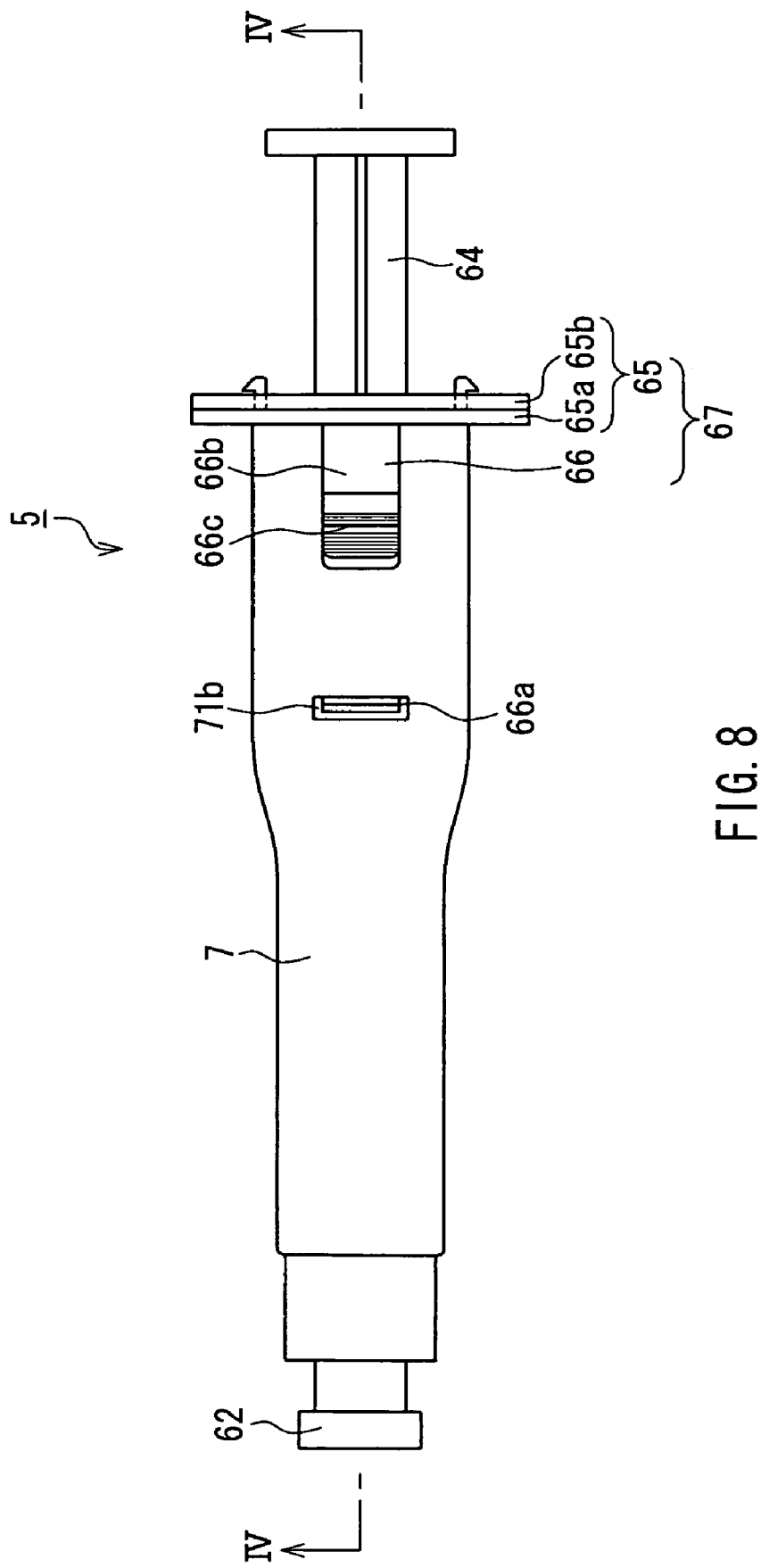
FIG. 8 is a side view showing an example of an injection device of Embodiment 2.
Figure 9:
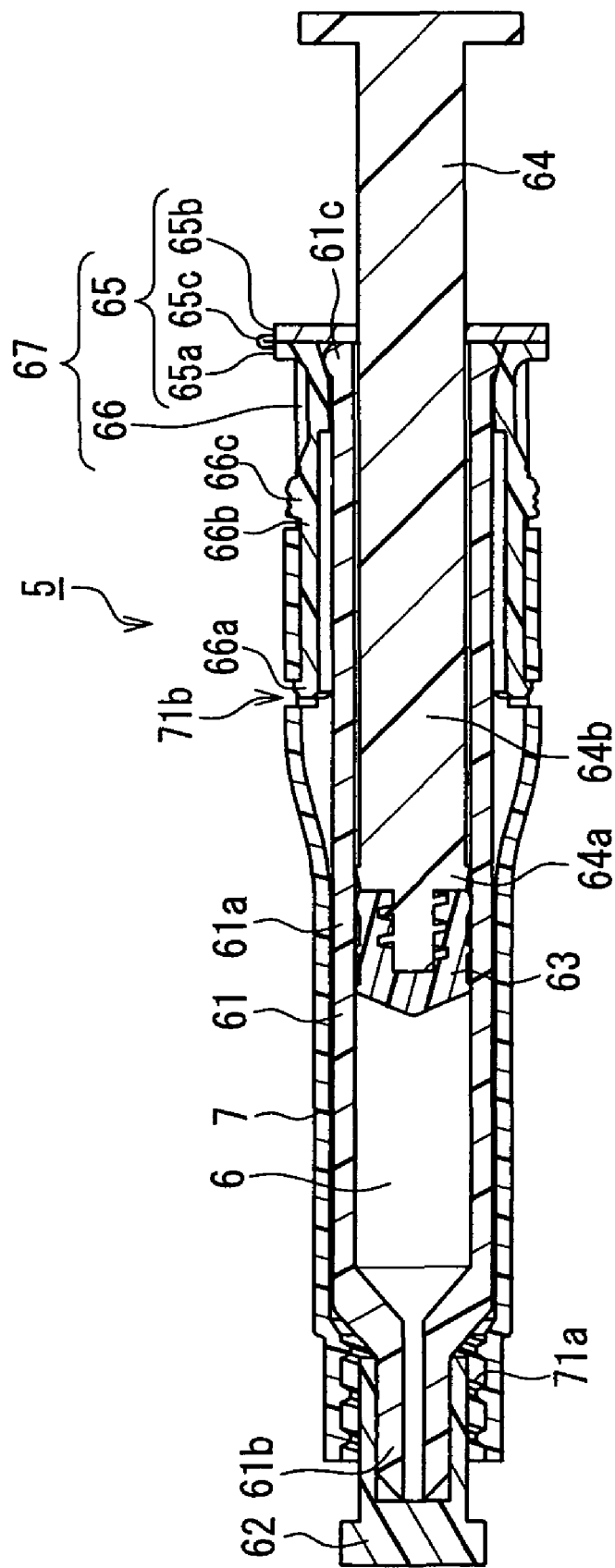
FIG. 9 is a cross-sectional view showing the injection device shown in FIG. 8, taken along a line IV-IV.
Figure 10:
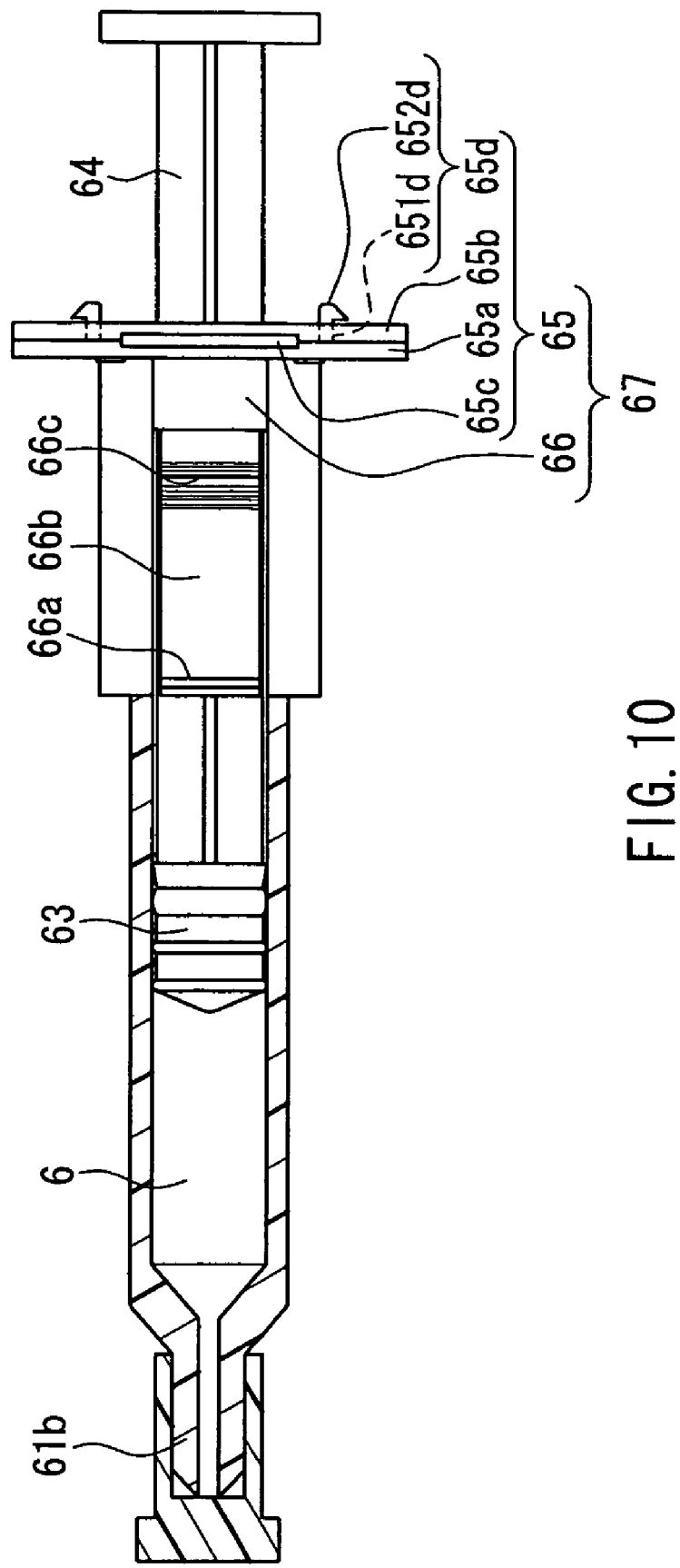
FIG. 10 is a partial cross-sectional view showing the injection device of FIG. 8 in a state where the holder is removed.

As shown in FIGS. 8 to 10, an injection device 5 of the present embodiment includes a prefilled syringe 6 and a holder 7 arranged to surround the outer periphery of a barrel 61 of the prefilled syringe 6. The barrel 61 includes a cylindrical barrel body 61a, and a nozzle 61b provided at the front end of the barrel and from which a drug solution or the like (not shown) charged in the barrel can be discharged. A cap 62 made of an elastic material such as rubber is put on an opening of the nozzle 61*b*, and thus the opening is closed. A gasket 63 is inserted slidably into the barrel 61 through a rear end opening of the barrel 61. The gasket 63 is connected with a plunger 64, and the plunger 64 can be placed into and removed from the barrel 61 through the rear end opening of the barrel 61.

The holder 7 has an inner diameter that allows the barrel body 61*a* to be inserted into the holder 7. A spiral protrusion 71*a* is formed on the inner surface of the holder 7 at a portion located around the nozzle 71*b*. The spiral protrusion 71*a* is formed so that it can be screwed with, for example, an injection needle or a female luer constituting a part of a three-way cock or the like.

Figure 12A:
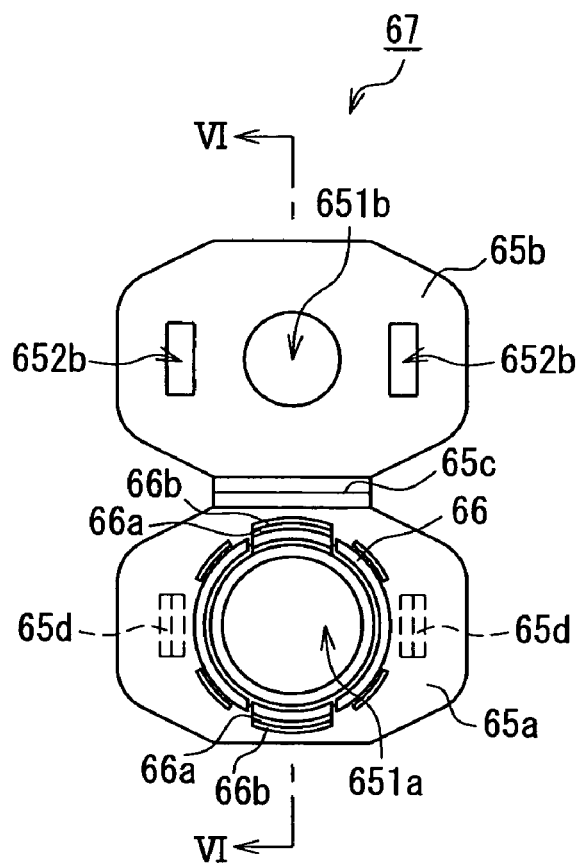
FIG. 12A is a view showing a structure including a finger flange and an erected portion and constituting the injection device of FIG. 8, viewed along the axial direction of the barrel.

As shown in FIG. 12A, a finger flange 65 (see FIG. 8 or the like) includes a first member 65*a* substantially in a plate shape, a second member 65*b* substantially in a plate shape, and a bendable hinge 65*c* for connecting the first and the second members. A pair of engagement openings 652*b* is formed on the second member 65*b* that constitutes the finger flange 65. In contrast, a pair of protrusions 65*d* corresponding to the pair of the engagement openings 652*b* is formed on the first member 65*a*. Each of the protrusions 65*d* is erected at a substantially right angle from a surface of the first member 65*a* that faces the second member 65*b*. As shown in FIG. 10, each of the protrusions 65*a* includes a leg portion 651*d* and a hook 652*d* provided at the tip of the leg portion. The length of the leg portion 651*d* is substantially equal to the thickness of the second member 65*b*.

In this manner, a holding structure constituting the finger flange 65 is configured of the engagement openings 652*b* and the protrusions 65*b*. The contact between the first member 65*a* and the second member 65*b* can be kept by inserting the protrusions 65*d* into the engagement openings 652*b*, and bringing the hooks 652*d* to face the surface of the second member 65*b* opposite to the surface facing the first member 65*a*.

As shown in FIGS. 10 and 12A, an erected portion 66 is linked to the first member 65*a*. A first hole 651*a* is formed on a portion between the pair of the protrusions 65*d*. It is preferable that the diameter of the first hole 651*a* is substantially equal to or slightly larger than the outer diameter of a large-diameter portion 61*c* (see FIG. 9) of the barrel body 61*a*. Further, it is preferable that the inner diameter at a part of the erected portion 66 is substantially equal to or larger than the outer diameter of the large-diameter portion 61*c*. In the example shown in FIG. 9, the inner diameter of the erected portion 66 at the base end portion is substantially equal to or larger than the outer diameter of the large-diameter portion 61*c*. Thus, the large-diameter portion 61*c* can be placed in the bore of the erected portion 66. Further, the inner diameter at a part of the erected portion 66 is substantially equal to or larger than the outer diameter of the large-diameter portion 61*c*, and the inner diameter at the other part of the erected portion 66 is smaller than the outer diameter of the large-diameter portion 61*c*. Thus, during the process for assembling the injection device of the present embodiment, the structure 67, which is attached to the barrel body 61*a* from the end of the nozzle 61*b* side and slid to the rear end side of the barrel body 61*a*, is prevented from passing through the large-diameter portion 61*c* and dropping off from the rear end side of the barrel body 61*a*.

In contrast, as shown in FIG. 12A, a second hole 651*b* is formed on the second member 65*b*. The second hole 651*b* is formed on a portion between the pair of the engagement openings 652*b*. It is preferable that the diameter of the second hole 651*b* is slightly smaller than the outer diameter of the front end portion 64*a* (see FIG. 9) of the plunger 64 but larger than the outer diameter of a portion 64*b* (see FIG. 9) located on the back side with respect to the front end 64*a* and is inserted in the barrel. In this case, it is possible to slide the plunger 64 smoothly, and the plunger 64 is prevented from dropping off.

Next, an engagement structure capable of keeping a state in which the holder 7 is attached to the barrel 61 and releasing the attachment will be described.

As shown in FIGS. 8 and 9, the engagement structure is configured of openings 71*b* formed by forming through holes that penetrate the cylinder wall of the holder 7 in the thickness direction, and engagement hooks 66*a* that is formed on the erected portion 66 and can be engaged with the openings 71*b*.

Figure 12B:
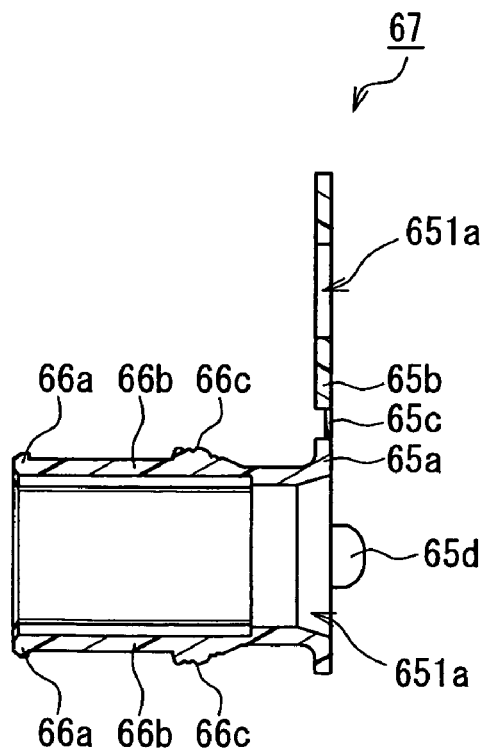
FIG. 12B is a cross-sectional view showing the structure shown in FIG. 12A, taken along a line VI-VI.

As shown in FIGS. 10, 12A and 12B, the erected portion 66 includes cantilever arms 66*b* having a free end on the front end side of the erected portion 66. The cantilever arms 66*b* are shaped as if they were formed by dividing a substantially cylindrical body into a plurality of pieces in the radial direction. Engagement hooks 66*a* protruding outwardly with respect to the erected portion 66 are formed on the free end side of the cantilever arms 66*b*.

There is no particular limitation for the number of the cantilever arms 66*b* as long as it matches the number of openings 71*b* formed on the holder 7. However, considering that the engagement is released with one hand, it is preferable that one or two cantilever arms are provided, and it is further preferable that two cantilever arms are provided. From the viewpoint of operability of releasing the engagement, it is further preferable that the pair of the cantilever arms 66*b* are formed at positions symmetrical to each other about the central axis of the erected portion 66.

There is no particular limitation for the positional relationship between the cantilever arms 66*b* and the protrusion 65*d*. For example, like the example shown in FIG. 12A, it is preferable that the pair of the cantilever arms 66*b* is formed on a straight line that is orthogonal to a straight line passing through the center of each of the protrusions 65*d* and the center of the first hole 651*a*, and that passes through the center of the first hole 651*a*, when the structure 67 is seen along the axial direction of the erected portion 66. That is, it is preferable that the cantilever arms 66*b* (engagement hooks 66*a*) and the protrusions 65*d* are apart from each other by a rotation angle of about 90 degrees.

Figure 11A:
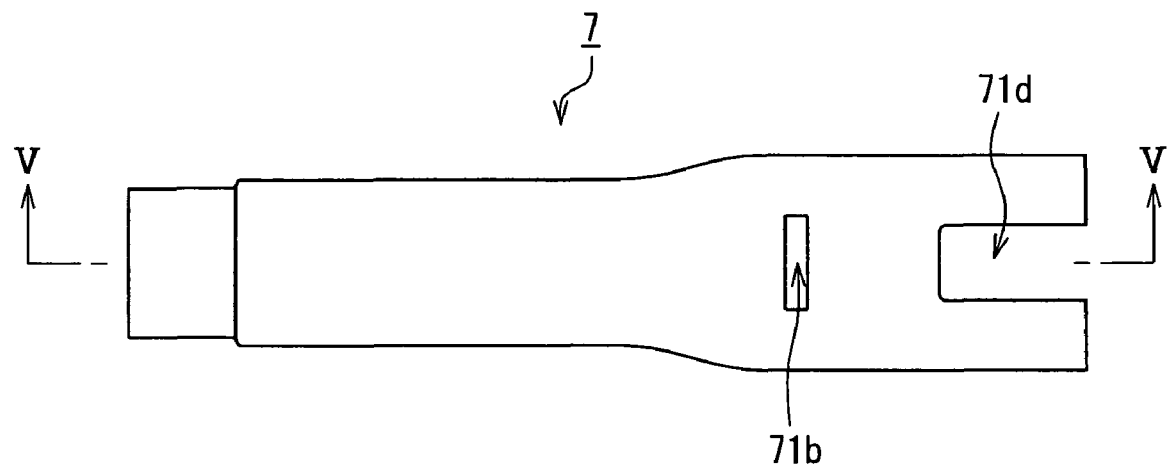
FIG. 11A is a side view showing the holder that constitutes the injection device shown in FIG. 8.
Figure 11B:
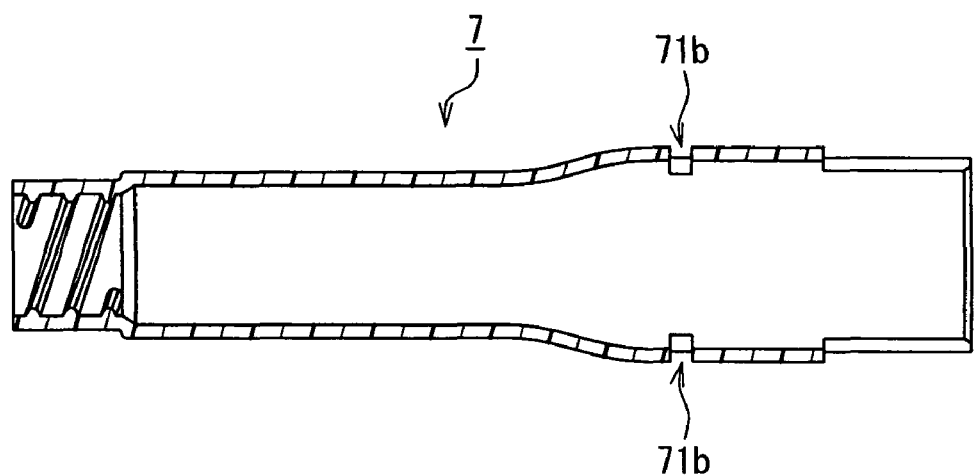
FIG. 11B is a cross-sectional view showing the holder shown in FIG. 11A, taken along a line V-V.

As shown in FIGS. 8, 11A and 11B, the holder 7 includes, at a portion closer to the base end than the openings 71*b*, notches 71*d* for exposing a portion of each of the cantilever arms 66*b*. By pressing the cantilever arms 66*b* exposed from the notches 71*d*, the engagement between the openings 71*b* and the engagement hooks 66 is released. It is preferable that a pressing protrusion 66*c* (see FIGS. 8 and 12A) is formed on each of the cantilever arms 66*b* at the portion exposed from the notch 71*d*. By pressing each of the pressing protrusions 66*c* in a direction toward the central axis of the holder 7 so as to bend the front end side of the cantilever arms 66*b*, a space between the front end side portions of the cantilever arms 66*b* is narrowed with the base end of each of the cantilever arms 66*b* as a fulcrum, and the engagement between each of openings 71*b* and the corresponding engagement hook 66*a* is released.

In this case, as shown in FIG. 9, a gap having a predetermined length is needed between each of the cantilever arms 66*b* and the barrel body 61*a* in order to bend the front end portions of the cantilever arms 66*b* as described above. However, it is preferable that the inner diameter of the holder 7 at the portion closer to the front end than the openings 71*b* is smaller than that at the portion closer to the rear end than the openings 71*b*. Furthermore, it is preferable that the inner diameter of the holder 7 at the portion closer to the front end than the openings 71b is slightly larger than the outer diameter of the barrel body 61a. In this case, each of the engagement hooks 66a formed on the respective cantilever arms 66b can be engaged with and released from the opening 71b, while the prefilled syringe 6 is prevented from wobbling in the radial direction within the holder 7.

Figure 13:
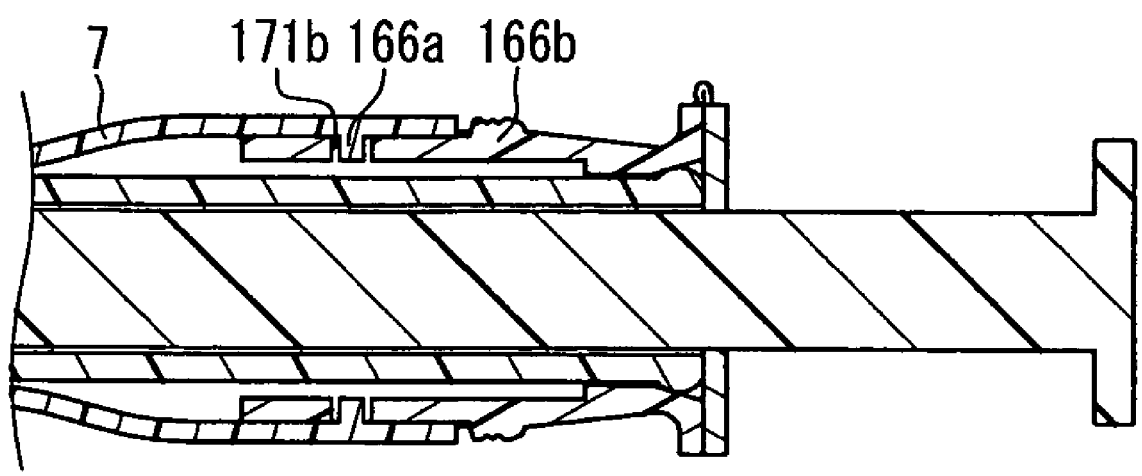
FIG. 13 is a side view showing a part of another example of the injection device of Embodiment 2.
Figure 14:
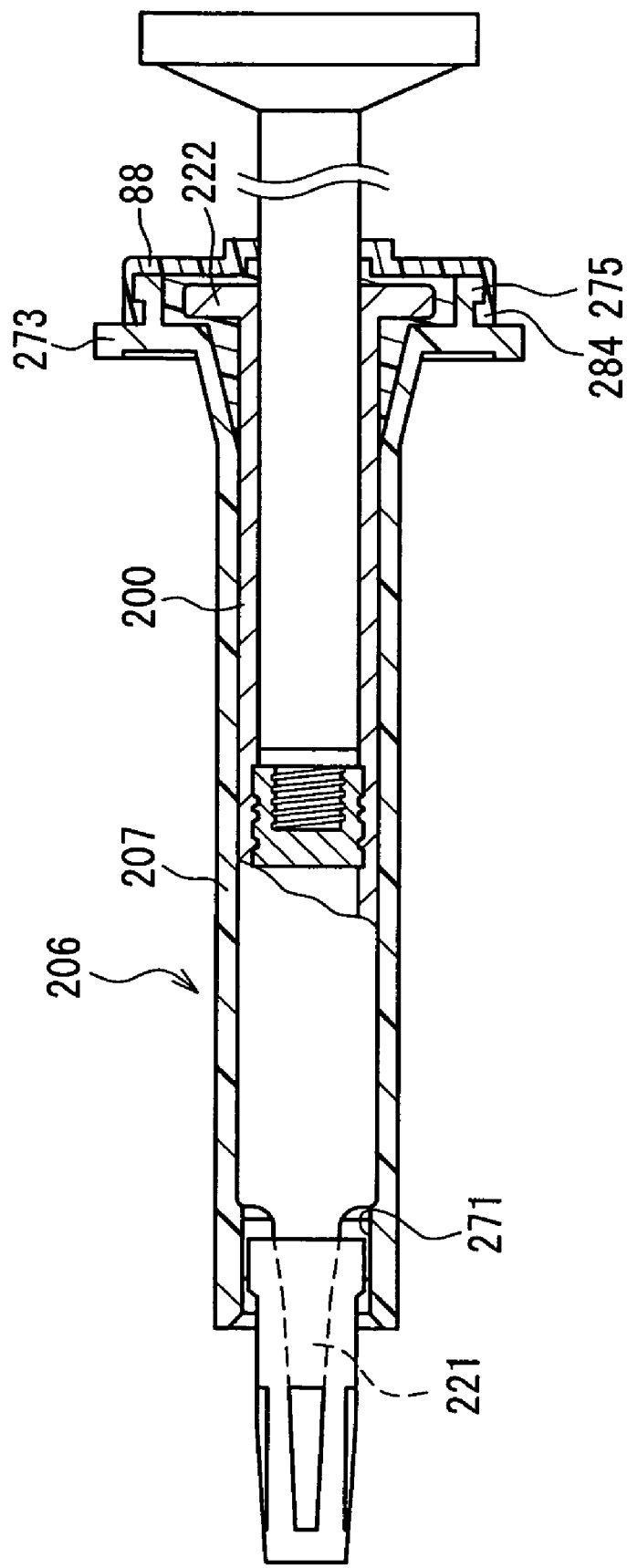
FIG. 14 is a side view showing an example of a conventional injection device.

As described above, in the example described with reference to FIGS. 8 to 12B, the engagement hooks 66a constituting the engagement structure are formed on the respective cantilever arms 66b, and the openings 71b with which the engagement hooks 66a engage are formed on the holder 7. The injection device of the present embodiment is not limited to such a form. For example, as shown in FIG. 13, engagement hooks 166a may be formed on the inner surface of the holder 7, and openings 171b may be formed on respective cantilever arms 166b.

As described above, in the example of the injection device of the present embodiment, the holder 7 can be freely attached to and detached from the prefilled syringe 6. As shown in FIG. 10, in a state where the engagement by the engagement structure is released and the holder 7 is detached from the prefilled syringe 6, the nozzle 61b can be inserted into, for example, an insertion hole formed on a valve provided with a mixed injection port.

Though a prefilled syringe is used as the syringe in Embodiments 1 and 2, the syringe may be an ordinary syringe including a barrel that is not filled with a drug solution in advance. The material of the barrel may be glass or a resin. When the material of the barrel is a resin, since the finger flange, the erected portion, engagement hooks, and the like can be molded simultaneously with the barrel body, they may be molded integrally with the barrel.

As described above, the injection device of the present invention includes the finger flange that is molded integrally with or separately from the barrel body, and the engagement structure capable of keeping a state in which the holder is attached to the barrel and releasing the attachment. Thus, the holder can be attached to and detached from the syringe, and the injection device can be operated stably even when the holder is detached from the syringe.

Accordingly, if the injection device is stored or carried in a state where the holder is attached to the syringe, breakage of the barrel can be prevented. By screwing, for example, a hub or the like of an injection needle with the spiral protrusion formed on the inner surface around the nozzle, an injection needle is prevented from dropping off in a case where a high pressure is applied to the injection needle or the like at the time of discharging a highly viscous medicine for example. Furthermore, by detaching the holder from the syringe as needed, the nozzle can be inserted into a mixed injection port or the like, which broadens the application range of the syringe.

INDUSTRIAL APPLICABILITY

In the injection device of the present invention, the holder can be freely attached to or detached from the barrel, and a state where the finger flange is provided in the vicinity of the rear end portion of the barrel is kept. Thus, the injection device can always be operated stably. As a result, the injection device can be applied in a broad range.

The invention claimed is:

1. An injection device comprising:
a syringe including a barrel including a cylindrical barrel body and a nozzle provided at a front end of the barrel body so as to be communicated with the barrel body, a gasket slidable in the barrel, and a plunger connected with the gasket and capable of being placed into and removed from the barrel through a rear end opening of the barrel;
a holder having an inner diameter that allows the barrel to be inserted in a bore of the holder, attached to the barrel, and including a spiral protrusion formed on an inner surface of a portion around the nozzle;
a finger flange provided in a vicinity of a rear end portion of the barrel body and molded separately from the holder and the barrel body;
an erected portion erected from the finger flange and attached to the barrel, the erected portion being molded separately from the holder and a portion of the barrel being placed in a bore of the erected portion;
an engagement structure capable of keeping a state in which the holder is attached to the barrel and releasing the attachment; and
a mechanism for keeping a state in which the finger flange and the erected portion are provided in the vicinity of the rear end portion of the barrel body,
wherein the engagement structure is adapted to engage the holder and the erected portion with each other and release the engagement between the holder and the erected portion, and
the engagement structure capable of keeping the state in which the holder is attached to the barrel and the mechanism for keeping the state in which the finger flange and the erected portion are provided in the vicinity of the rear end portion of the barrel body are independent from each other,
wherein the engagement structure includes: an opening formed on either the holder or the erected portion; and an engagement hook formed on either the holder or the erected portion on which the opening is not formed and capable of engaging with the opening,
wherein the opening is formed on the holder and the engagement hook is formed on the erected portion,
wherein the opening is formed on a rear end side of the holder,
wherein the holder includes, on the rear end side thereof, a bendable strip, a central portion of the bendable strip being linked to the other part of the holder and supporting the bendable strip, and the opening is formed on the bendable strip at a portion closer to the finger flange than the support portion, and
wherein the finger flange includes:
a first member linked to the erected portion and including a first hole formed thereon;
a second member including a second hole formed thereon; and
a holding structure for keeping a state in which the second member is disposed on a side of the first member opposite to a side facing the erected portion so that the second hole communicates with the first hole, and
the holding structure includes:
an engagement opening provided on either the first member or the second member; and
a protrusion formed on either the first member or the second member on which the engagement opening is not formed and capable of engaging with the engagement opening.

2. The injection device according to claim 1, wherein an outer surface of the bendable strip and a peripheral surface of the holder around the bendable strip are in the same circumferential plane.

3. An injection device, comprising:
a syringe including a barrel including a cylindrical barrel body and a nozzle provided at a front end of the barrel body so as to be communicated with the barrel body, a gasket slidable in the barrel, and a plunger connected with the gasket and capable of being placed into and removed from the barrel through a rear end opening of the barrel;
a holder having an inner diameter that allows the barrel to be inserted in a bore of the holder, attached to the barrel, and including a spiral protrusion formed on an inner surface of a portion around the nozzle;
a finger flange provided in a vicinity of a rear end portion of the barrel body and molded separately from the holder and the barrel body;
an erected portion erected from the finger flange and attached to the barrel, the erected portion being molded separately from the holder and a portion of the barrel being placed in a bore of the erected portion;
an engagement structure capable of keeping a state in which the holder is attached to the barrel and releasing the attachment; and
a mechanism for keeping a state in which the finger flange and the erected portion are provided in the vicinity of the rear end portion of the barrel body,
wherein the engagement structure is adapted to engage the holder and the erected portion with each other and release the engagement between the holder and the erected portion, and
the engagement structure capable of keeping the state in which the holder is attached to the barrel and the mechanism for keeping the state in which the finger flange and the erected portion are provided in the vicinity of the rear end portion of the barrel body are independent from each other,
wherein the engagement structure includes: an opening formed on either the holder or the erected portion; and an engagement hook formed on either the holder or the erected portion on which the opening is not formed and capable of engaging with the opening,
wherein the erected portion includes a cantilever arm having a free end on the front end side of the erected portion, and the engagement hook is formed on the free end side of the cantilever arm, and
wherein the finger flange includes:
a first member linked to the erected portion and including a first hole formed thereon;
a second member including a second hole formed thereon; and
a holding structure for keeping a state in which the second member is disposed on a side of the first member opposite to a side facing the erected portion so that the second hole communicates with the first hole, and
the holding structure includes:
an engagement opening provided on either the first member or the second member; and
a protrusion formed on either the first member or the second member on which the engagement opening is not formed and capable of engaging with the engagement opening.

4. The injection device according to claim 3, wherein
the holder includes, at a portion closer to the rear end than the opening, a notch from which a portion of the cantilever arm can be exposed, and
engagement between the opening and the engagement hook can be released by pressing the portion of the cantilever arm exposed from the notch.

5. The injection device according to claim 4, wherein a pressing protrusion is formed on the cantilever arm at the portion exposed from the notch.

6. An injection device, comprising:
a syringe including a barrel including a cylindrical barrel body and a nozzle provided at a front end of the barrel body so as to be communicated with the barrel body, a gasket slidable in the barrel, and a plunger connected with the gasket and capable of being placed into and removed from the barrel through a rear end opening of the barrel;
a holder having an inner diameter that allows the barrel to be inserted in a bore of the holder, attached to the barrel, and including a spiral protrusion formed on an inner surface of a portion around the nozzle;
a finger flange provided in a vicinity of a rear end portion of the barrel body and molded separately from the holder and the barrel body;
an erected portion erected from the finger flange and attached to the barrel, the erected portion being molded separately from the holder and a portion of the barrel being placed in a bore of the erected portion;
an engagement structure capable of keeping a state in which the holder is attached to the barrel and releasing the attachment; and
a mechanism for keeping a state in which the finger flange and the erected portion are provided in the vicinity of the rear end portion of the barrel body,
wherein the engagement structure is adapted to engage the holder and the erected portion with each other and release the engagement between the holder and the erected portion, and
the engagement structure capable of keeping the state in which the holder is attached to the barrel and the mechanism for keeping the state in which the finger flange and the erected portion are provided in the vicinity of the rear end portion of the barrel body are independent from each other,
wherein the engagement structure includes: an opening formed on either the holder or the erected portion; and an engagement hook formed on either the holder or the erected portion on which the opening is not formed and capable of engaging with the opening, and
wherein the finger flange includes:
a first member linked to the erected portion and including a first hole formed thereon;
a second member including a second hole formed thereon; and
a holding structure for keeping a state in which the second member is disposed on a side of the first member opposite to a side facing the erected portion so that the second hole communicates with the first hole, and
the holding structure includes:
an engagement opening provided on either the first member or the second member; and
a protrusion formed on either the first member or the second member on which the engagement opening is not formed and capable of engaging with the engagement opening.

7. The injection device according to claim 6, wherein the first member and the second member are connected with each other via a hinge.

8. The injection device according to claim 6, wherein the engagement opening is formed on the first member, and the protrusion is formed on the second member.

* * * * *